United States Patent

Ahlgren et al.

[11] Patent Number: 6,117,452
[45] Date of Patent: Sep. 12, 2000

[54] FATTY ESTER COMBINATIONS

[75] Inventors: Nils Ahlgren, Plainsboro, N.J.; Joseph Cascone, Chantilly, Va.; Joan Fitzpatrick, Ashburn, Va.; Steven E. Frisbee, Reston, Va.; John Getz, Clearwater, Fla.; Mark R. Herman, Nokesville, Va.; Bernard M. Kiernan, Ashburn, Va.; Barbara Montwill, Fairfax, Va.; Ed O'Donnell, Danbury, Conn.; Desiree Pereira, Fairfax, Va.; Pradeepkumar P. Sanghvi, Herndon, Va.

[73] Assignee: Fuisz Technologies Ltd., Chantilly, Va.

[21] Appl. No.: 09/132,922

[22] Filed: Aug. 12, 1998

[51] Int. Cl.[7] .................. A61K 9/26; A61K 9/16; A61K 9/50
[52] U.S. Cl. .................. 424/468; 424/469; 424/489; 424/490; 424/494; 424/502; 424/495
[58] Field of Search .................. 424/489, 490, 424/494, 502, 468, 469, 495

[56] References Cited

U.S. PATENT DOCUMENTS

| 4,132,753 | 1/1979 | Blichare et al. ............ 264/25 |
|---|---|---|
| 4,837,381 | 6/1989 | Steber et al. ............ 424/502 |
| 4,871,777 | 10/1989 | Breitzke ............ 514/785 |
| 4,880,634 | 11/1989 | Speiser ............ 424/450 |
| 4,970,081 | 11/1990 | Frisbee . |
| 5,011,532 | 4/1991 | Fuisz . |
| 5,169,645 | 12/1992 | Shukla et al. ............ 424/499 |
| 5,213,810 | 5/1993 | Steber . |
| 5,234,695 | 8/1993 | Hobbs et al. ............ 424/489 |
| 5,433,951 | 7/1995 | Serajuddin et al. . |
| 5,567,439 | 10/1996 | Myers et al. . |
| 5,571,533 | 11/1996 | Santus et al. ............ 424/469 |
| 5,840,334 | 11/1998 | Raiden et al. . |
| 5,851,555 | 12/1998 | Sanghvi et al. . |
| 5,869,098 | 2/1999 | Misra et al. . |
| 5,876,749 | 3/1999 | Al-Razzak et al. . |
| 5,883,103 | 3/1999 | Burnside et al. . |
| 5,895,664 | 4/1999 | Cherukuri et al. . |

*Primary Examiner*—Thurman K. Page
*Assistant Examiner*—P. McQueeney
*Attorney, Agent, or Firm*—Richard D. Schmidt

[57] ABSTRACT

The thermoforming of compositions containing active agents is carried out by processing compositions containing certain fatty esters in combination.

29 Claims, No Drawings

FATTY ESTER COMBINATIONS

FIELD OF THE INVENTION

The invention deals with the preparation of thermoformed particulates of active agents via processes, which employ certain combinations of fatty esters and optional surfactants or emulsifiers as processing aids.

SUMMARY OF THE INVENTION

Particulates containing active agents are commonly used in comestible units containing pharmaceuticals and foods to promote consumer acceptance. Microspheres are preferred particulates because they are easy to process and they can be readily treated, e.g., with taste-masking and/or controlled release coatings.

Applicants have discovered that certain fatty esters, surfactants and optional emulsifiers are useful in making such microspheres.

BACKGROUND

The use of fatty esters, alone and in combinations, in pharmaceutical formulations is known.

U.S. Pat. No. 4,837,381 to Steber et al discusses microspheres made from mixtures of active agents with optional surfactants and fat, wax or mixtures thereof. Glyceryl stearate is shown at column 3, lines 10–11. Polyoxyethylene (23) stearate is mentioned at column 6, line 45. The ingredients can be processed into microspheres via melt blending and cooling, e.g., using a centrifugal disc (see column 5, lines 32+).

U.S. Pat. No. 4,880,634 to Speiser shows monopellets containing melt-blended combinations of lipids and surfactants. Glyceryl stearate esters and GELUCIRE are disclosed at column 4. U.S. Pat. No. 5,571,533 to Santus deals with the melt blending of drugs with glycerides (col. 5, line 46) and GELUCIRES (col. 5, line 24), followed by granulation.

U.S. Pat. No. 4,132,753 to Blichare et al deals with sustained release granules made by exposing a mixture of powdered active agents with particles of a wax-like material to radiation heating. Glyceryl monostearate is recited at column 3, line 14.

U.S. Pat. No. 4,871,777 to Breitzke refers to suppositioning bases made by melt blending fats and emulsifiers.

U.S. Pat. No. 5,234,695 to Hobbs et al describes a free flowing powder made by blending a low viscosity mixture of vitamin E compound with a fatty acid ester and then spraying the blend.

U.S. Pat. No. 5,169,645 to Shukla et al shows the preparation of granules containing drugs, waxes and polymeric wax modifiers by melt processing.

THE INVENTION

The invention deals with compositions and processes that use fatty ester combinations and optional surfactants or emulsifier(s) as processing aids in the production of particulates, microspheres containing active agent(s). The particulates made especially are disclosed and claimed.

The fatty esters are glyceryl monostearate and polyethylene glycol (32) glyceryl palmitystearate.

DETAILED DESCRIPTION OF THE INVENTION

Unless otherwise stated, all percentages herein are weight percents, based upon total composition weight. All publications and patent applications referred to are hereby incorporated by reference.

The invention deals with the thermoprocessing of compositions containing active agent(s) and combinations of processing aid(s), as well as with the particulates made by that thermoprocessing.

The particulates may be mixed with various excipients and treated with coatings, as described below.

Compositions for Making Particulates

The compositions to be processed contain:
(a) one or more active agents;
(b) a combination of processing aids consisting essentially of:
  (1) glyceryl monostearate, and
  (2) polyethylene glycol (32) glyceryl palmitostearate, and
  (3) one or more optional emulsifiers and/or surfactants.

Particulates made therefrom may be called "microparticles" and preferably microspheres having average particles diameters of about 150 to about 300 microns.

The compositions from which microspheres are made contain each of these ingredients in the following ranges:

|  | Broad | Preferred Ranges (I) | (II) | (III) |
|---|---|---|---|---|
| Active agent(s) | 5–90% | 65–90% | 40–65% | 5–40% |
| Glyceryl monostearate | 14–90% | 10–25% | 30–55% | 65–90% |
| PEG (32) glyceryl palmitostearate | 2–15% | 2–6% | 5–15% | 5–10% |
| Emulsifier(s)/Surfactants | 0–10% | 1–4% | 0–10% | 0–10% |

As the table above indicates, the amounts of drug and processing aid combination used vary. Generally, however, useful quantity ranges fall into three compositional categories, labeled (I), (II), and (III), depending upon the amount of the active agent(s) used.

Applicants do not wish to be bound by any particular theory. However, the physiochemical properties of the active agent and its concentration in the particulates of the invention seems to control the amount of fatty esters and optional emulsifier(s) and/or surfactants to be used. Other factors which affect the amount of fatty esters are melting points, viscosities of molten materials, HLB values, and dissolution profile.

The quantity of glyceryl monostearate used varies inversely to the loading of active agent(s). Low amounts of stearate are used with high amounts of active agents.

Within each category, there are highly preferred loadings of active agent(s). Thus, for category (I), drug loadings of about 70 to about 80% are highly preferred. For category (II), drug loadings of about 40% to about 50% are best. For category (III), drug loadings of about 20 to about 30% are most desirable.

For category (I) compositions, the active agents are exemplified by ibuprofen, cimetidine and fexofenadine. Mixtures are operable.

In (I) combinations, the total amount of processing aid is kept at levels of about 35% or less. Levels of about 15 to about 30 are preferred.

For category (II) combinations, the total amount of processing aid is between about 35% and about 70%, with levels of about 40 to about 60 preferred. Exemplary category (II) active agents include fexofenadine and the like.

For category (III) compositions, the active agents can be represented by dextromethorphan HBr. Other agents in this category include chlorpheniramine maleate and famotidine. Mixtures can be used.

For the category (III) compositions, the total level of spheronization aid lies between 65 and 90%, with levels of about 65 to about 80 preferred.

Active Agents

The active agents useful herein can be selected from a large group of bio-affecting or therapeutic agents. They include those in the following therapeutic categories: ace-inhibitors; alkaloids; antacids; analgesics; anabolic agents; anti-anginal drugs; anti-allergy agents; anti-arrhythmia agents; antiasthmatics; antibiotics; anticholesterolemics; anticonvulsants; anticoagulants; antidepressants; antidiarrheal preparations; anti-emetics; antihistamines; antihypertensives; anti-infectives; anti-inflammatories; antilipid agents; antimanics; anti-migraine agents; antinauseants; antipsychotics; antistroke agents; antithyroid preparations; anabolic drugs; antiobesity agents; antiparasitics; antipsychotics; antipyretics; antispasmodics; antithrombotics; antitumor agents; antitussives; antiulcer agents; anti-uremic agents; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others.

Active agents which may be used in the invention include: acetaminophen; acetic acid; acetylsalicylic acid, including its buffered forms; acrivastine; albuterol and its sulfate; alcohol; alkaline phosphatase; allantoin; aloe; aluminum acetate, carbonate, chlorohydrate and hydroxide; alprozolam; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diproprionate; benzocaine; benzoic acid; benzophenones; benzoyl peroxide; benzquinamide and its hydrochloride; bethanechol; biotin; bisacodyl; bismuth subsalicylate; bornyl acetate; brompheniramine and its maleate; buspirone; caffeine; calamine; calcium carbonate, casinate and hydroxide; camphor; captopril; cascara sagrada; castor oil; cefaclor; cefadroxii; cephalexin; centrizine and its hydrochloride; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleates and tannates; chlorpromazine; cholestyramine resin; choline bitartrate; chondrogenic stimulating protein; cimetidine and its hydrochloride; cinnamedrine hydrochloride; citalopram; citric acid; clarithromycin; clemastine and its fumarate; clonidine and its hydrochloride salt; clorfibrate; cocoa butter; cod liver oil; codeine and its fumarate and phosphate; cortisone acetate; ciprofloxacin HCl; cyanocobalamin; cyclizine hydrochloride; cyproheptadine and its hyddrochloride; danthron; dexbromopheniramine maleate; dextromethorphan and its hydrohalides; diazepam; dibucaine; dichloralphenazone; diclofen and its alkali metal sales; diclofenac sodium; digoxin; dihydroergotamine and its hydrogenates/mesylates; diltiazem; dimethicone; dioxybenzone; diphenhydramine and its citrate; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; fluoxetine; folic acid; fosphenytoin; 5-fluorouracil (5-FU); fluoxetine and its hydrochloride; flurbiprofen; furosemide; gabapentan; gentamicin; gemfibrozil; glipizide; glycerine; glyceryl stearate; granisetron and its hydrochloride; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isosorbide and its mono- and dinitrates; isoxicam; ketamine; kaolin; ketoprofen; lactic acid; lanolin; lecithin; leuprolide acetate; lidocaine and its hydrochloride salt; lifinopril; liotrix; loratadine; lovastatin; luteinizing hormore; LHRH (lutenizing hormone replacement hormone); magnesium carbonate, hydroxide, salicylate, and trisilicate; meclizine and its hyddrochloride; mefenamic acid; meclofenamic acid; meclofenamate sodium; medroxyprogesterone acetate; methenamine mandelate; menthol; meperidine hydrochloride; metaproterenol sulfate; methscopolamine and its nitrates; methsergide and its maleate; methyl nicotinate; methyl salicylate; methyl cellulose; methsuximide; metoclopramide and its halides/hydrates; metronidazole and its hydrochloride; metoprotol tartrate; miconazole nitrate; mineral oil; minoxidil; morphine; naproxen and its alkali metal sodium salts; nifedipine; neomycin sulfate; niacin; niacinamide; nicotine; nicotinamide; nimesulide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron and its hydrochloride; oxolinic acid; oxybenzone; oxtriphylline; para-aminobenzoic acid (PABA); padimate-O; paramethadione; pentastatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine and its hydrochloride salt; phenytoin; pirmenol; piroxicam and its salts; polymicin B sulfate; potassium chloride and nitrate; prazepam; procainamide hydrochloride; procaterol; promethazine and its hydrochloride; propoxyphene and its hydrochloride and napsylate; pramiracetin; pramoxine and its hydrochloride salt; prochlorperazine and its maleate; propanolol and its hydrochloride; promethazine and its hydrochloride; propanolol; pseudoephedrine and its sulfates and hydrochorides; pyridoxine; pyrolamine and its hydrochlorides and tannates; quinapril; quinidine gluconate and sulfate; quinestrol; ralitoline; ranitadine; resorcinol; riboflavin; salicylic acid; scopolamine; sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; theophylline; terfenadine; thiethylperazine and its maleate; timolol and its maleate; thioperidone; tramadol; trimetrexate; triazolam; tretinoin; tetracycline hydrochloride; tolmetin; tolnaftate; triclosan; trimethobenzamide and its hydrochloride; tripelennamine and its hydrochloride; tripolidine hydrochloride; undecylenic acid; vancomycin; verapamil HCl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Mixtures and pharmaceutically acceptable salts of these and other actives can be used.

Particularly useful active agents are sparingly soluble solid agents whose dissolution and release properties are enhanced by the solubilizing agents used herein. These agents include $H_2$ antagonists, analgesics, including non-steroidal anti-inflammatory drugs (NSAIDs), anticholesterolemics, anti-allergy agents, and anti-migraine agents.

Analgesics include aspirin, acetaminophen, acetaminophen plus caffeine, and non-steroidal anti-inflammatory drugs (NSAIDS), e.g., ibuprofen and nimesulide.

Useful NSAIDs include ibuprofen; diclofenac and its alkali metal salts; fenoprofen and its metal salts; fluriprofen; ketoprofen; naproxen and its alkali metal salts; nimesulide; and piroxicam and its salts.

$H_2$-antagonists which are contemplated for use in the present invention include cimetidine, ranitidine hydrochloride, famotidine, nizatidine, ebrotidine, mifentidine, roxatidine, pisatidine and aceroxatidine.

Useful anti-allergy agents include hydricodone and its tartrates; clemastine and its fumarate; azatadine and its maleate; acetaminophen; hydroxyzine and its pamoate and hydrochloride salts; chlorpheniramine and its maleates and tannates; pseudoephedrine and its sulfates and hydrochlorides; bromopheniramine and its maleate; dextromethorphan and its hydrohalides; loratadine; phenylephrine and its tannates and hydrochlorides; methscopolamine and its nitrates; phenylpropanolamine and its hydrochlorides; codeine and its hydrochloride; codeine and its phosphate; terfenadine; acrivastine; astemizole; cetrizine and its hydrochloride; phenindamine and its tartrate; tripelennamine and its hydrochloride; cyproheptadine and its hydrochloride; promethazine and its hydrochloride; and pyrilamine and its hydrochlorides and tannates.

Useful antimigraine agents include divalproex and its alkali metal salts; timolol and its maleate; propanolol and its hydrohalides; ergotamine and its tartrate; caffeine; sumatriptan and its succinate; dihydroergotamine, its hydrogenates/mesylates; methsergide and its maleate; isometheptene mucate; and dichloralphenazone.

Another class of drugs which can be used are antiemetics. Useful antiemetics include: meclizine and its hydrochloride; hydroxyzine and its hydrochloride and pamoate; diphenhydramine and its hydrochloride; prochlorperazine and its maleate; benzquinamide and its hydrochloride; granisetron and its hydrochloride; dronabinol; bismuth subsalicylate; promethazine and its hydrochloride; metoclopramide and its halides/hydrates; chlorpromazine; trimethobenzamide and its hydrochloride; thiethylperazine and its maleate; scopolamine; perphenazine; and ondansetron and its hydrochloride.

Other active ingredients for use in the present invention include antidiarrheals such as immodium AD, antihistamines, antitussives, decongestants, vitamins, and breath freshners. Also contemplated for use herein are anxiolytics such as Xanax; antipsychotics such as Clozaril and Ilaldon; antihistamines such as Seldane, Hismanal, Relafen, and Tavist; antiemetics such as Kytril and Cesamet; bronchodilators such as Bentolin, Proventil; antidepressants such as Prozac, Zoloft, and Paxil; antimigranes such as Imigran, ACE-inhibitors such as Vasotec, Capoten and Zestril; Anti-Alzheimers agents such as Nicergoline; and $Ca^{11}$-Antagonists such as Procardia, Adalat, and Calan.

Among the anticholesterolemics, the statins, e.g., lovastatin, provastatin and the like are notable.

Combinations of various types of drugs, as well as combinations of individual drugs, are contemplated.

Processing Aids

Glyceryl monostearate, commercially available as MYVAPLEX 600, GMS, IMWITOR, and SIMULSOLI 65, is the monoester of 1, 2, 3-propane-triol with octadecanoic acid. It has been used as a nonionic emulsifier, stabilizer, emollient, plasticizer and lubricant.

Polyethylene glycol (32) glyceryl palmitostearatc is sold as GELUCIRE 50/13 by Gattefosse S. A. (France). It is a mixture of mono-, di- and triglycerides and polyethylene glycol mono- and diesters.

The optional emulsifiers/surfactants useful in the invention are selected from sodium lauryl sulfate, Poloxamers, Tweens, and Spans. Sodium lauryl sulfate and Poloxamer 188 are preferred.

Excipients

Excipients useful herein include a wide variety of additives, or ingredients, conventionally used in comestible units in which particulates may be employed.

The floss, or matrix particles, described below are highly useful forms in which excipients can be used.

Orally ingestible units, e.g., tablets, pills, capsules, troches, and liquid suspensions are preferred. However, transdermal, buccal, and nasal products are contemplated.

The nature of the final product will determine the quantities and types of excipients used.

For comestible units, the excipients which may be used include: sweeteners, flavors, perfumes, stabilizers, flow control agents, colorants, glidants, filler, diluents (solid and liquid), solubilizers, lubricants, effervescent agents and the like. The use of multiple agents of each type is contemplated.

Coatings

The microspheres made herein may be substrates for one or more coatings which enhance consumer acceptability, e.g., mask taste and control drug delivery.

Useful taste-masking coatings include polymeric materials. Cellulosic polymers are useful. Mixtures are operable.

Controlled release coatings include those which yield, for example, enteric release, sustained release or pulsatile release. Useful coatings include ethylcellulose, polymethacrylates, and wax, respectively.

Depending upon the function of the coatings, coating levels -i.e., tablet weight increases—of about 5 to about 100%, preferably 5% to 40% based on microsphere weight, are operable. Multiple coatings can be employed.

Coatings are generally applied to the microspheres of the invention using conventional coating devices, such as fluid bed coaters.

Procedures for Making Particulates

The particulates are typically microspheres made via a spheronization process and using suitable thermoprocessing or thermoforming conditions. In general, thermoforming techniques which employ processing parameters similar to those described here may be used.

Microspheres can be made using spinning devices and processes described in U.S. Pate. Nos. 5,458,823 and 5,638,720 and U.S. patent application Ser. No. 08/874,215 filed Jun. 13, 1997 now U.S. Pat. No. 5,851,454.

Particulates can also be made using extruders and other thermoforming devices.

These disclosures and others described in patents and applications assigned to applicant's assignee, Fuisz Technologies, Ltd., relate to the use of "liquiflash conditions" to produce discrete particles having different morphologies from those of the starting materials from which they are formed.

"Liquiflash conditions" are generally those under which the material, called a feedstock, is rapidly heated just to the point at which it undergoes intraparticulate flow and partially deforms or liquifies so that it can pass through openings in a suitable spinning device. The passage of the liquiflash particles through openings is in response to centrifugal forces within the spinning head, which forces "expel" the particles, as discrete solids out of the device and into the atmosphere. The expelled materials instantly reform into particles, without the application of external shaping forces, which particles have different morphologies, i.e., internal crystalline character, from those of the feedstocks.

Because heat-sensitive active agents are sometimes used, it is often desirable to use devices which ensure that the amount of time that the agent(s) are exposed to heat is kept to a minimum. Also, it is preferred that the materials not be heated beyond the point at which they reach liquiflash conditions.

Applicants have found that one particular spinning device is highly useful in making the microspheres of the invention. In U.S. Pat. No. 5,458,823, a spinning device is described which uses a spinning head including a base and a cover. A plurality of closely spaced heating elements are positioned between the base and cover, forming a barrier through which the material to be processed passes. In use, the head rotates and the heating elements are heated to temperatures which bring about liquiflash conditions in the materials being processed. As the spinning head rotates, the centrifugal force created by its rotation expels the material through spaces between the heating elements. The material forms discrete, generally spherical particles as it exits.

The production of microspheres for use in the subject invention may be optimized by the use of a V-groove insert inside the spinner head. The insert is described in pending U.S. patent application Ser. No. 08/874,215, filed Jun. 13, 1997 now U.S. Pat. No. 5,851,454. The insert has grooves therein, which grooves have a uniform depth and width through their length, so that highly uniform discrete microspheres or other particles are produced. Using this or a similar insert, the spinning device is operated at 50 to 75 Hz, at about 10 to 25% power, and at temperatures which yield liquiflash conditions.

It should be noted that "liquiflash conditions" vary with the properties of the material, or feedstock, being processed. Since the feedstocks contain many substances in varying amounts, the parameters need to yield "liquiflash conditions" for a particular mixture must be ascertained by processing small quantities or samples before processing large ones. Typically, the feedstocks contain active agent(s) and processing aids.

Character and Use of Particulates

While particulates made using various thermoprocessing technologies are useful, microspheres described below are preferred.

The microspheres or other particulates are generally solid spherical bodies of about 150 to about 200 microns mean particle diameter.

It is preferred that they be produced via a direct spheronization process, such as liquiflash or other suitable techniques. However, they may be made by physically altering the size and/or shape of non-spherical particles by extrusion/spheronization of melt granulation processes.

When microspheres are made by direct spherorization of compositions containing active agent(s), the fatty esters and optional emulsifiers/surfactants, the fatty esters function as spheronization aids.

The microspheres may be used as is, i.e., in powder or sachet products for delivering active agents. Alternatively, they may be used in the production of solid, liquid (suspensions), or semi-solid (e.g., gel-like) comestible units, etc. Tablets and capsules are preferred.

It is preferred that the microspheres of the invention be used in combination with excipients which have been formed into floss or matrix particles. Useful flosses are generally made from saccharide based carriers. See U.S. Pat. Nos. 5,622,719 and 5,587,172.

Once the floss and microsphere ingredients are combined, they can be shaped into comestible units.

EXAMPLES

The following examples illustrate the invention. Example I shows an embodiment in which emulsifiers are used along with fatty esters.

Example I

Cimetidine Microspheres

A spinning device of the type disclosed in U.S. Ser. No. 08/874,215, filed Jun. 13, 1997 and now U.S. Pat. No. 5,851,454 and having a 3-inch head was used to make microspheres from the following composition:

| | |
|---|---|
| Cimetidine | 70% |
| Gelucire 50/13 | 5% |
| Myvaplex 600P | 22.5% |
| Sodium lauryl sulfate | 2.5% |

The composition was processed at about 135° C., 70% duty cycle and at 60Hz (3600 rpm). The microspheres were collected and sieved through #60 mesh and onto 140 mesh.

Dissolution tests showed the microspheres to release 93% of the cimetidine within 15 minutes.

The microspheres were then coated for taste masking on a Niro MP-1 fluidized bed coater with 30% coating. The coating contained an ethyl cellulose/hydroxypropyl cellulose blend (1:1) in acetone/isopropyl alcohol solvent system.

The coated microspheres are used in the following tablet formulation:

| | |
|---|---|
| Cimetidine Coated Microshperes | 41.27% |
| Floss (0.5% ethanol treated)* | 49.48% |
| Flavor | 1.50% |
| Citric Acid | 2.00% |
| Mannitol | 5.00% |
| Syloid | 0.25% |
| Sodium Stearyl Fumarate | 0.50% |

*The floss component was produced in accordance with Example VI of U.S. application Ser. No. 08/915,068, filed August 20, 1997, now U.S. Pat. No. 5,840,334. The floss was sprayed with 0.5% ethanol and dried before it was used in the cimetidine tablet formulation.

The tablets were made on a Kilian Rotary Tablet press using 12 mm flat faced tooling at 1.0–2.0 lb. hardness and a tablet weight of 450mg.

Examples IIA and IIB

Ibuprofen (IBP) Microspheres

Using similar procedures, microspheres were made from compositions containing:

|   | A | B |
|---|---|---|
| IBP | 78% | 88% |
| Myvaplex 600P | 16% | 10% |
| Gelucire 50/13 | 6% | 2% |

Formulation A was processed using the device of Example 1.

Formulation B was processed in a 5-inch head of the type disclosed in Ser. No. 08/874,215, at 20% capacity and 60Hz.

Other microspheres were made using various amounts of IBP and other ingredients as follows:

| Ibuprofen | 65–90% |
|---|---|
| Myvaplex 600P | 10–25% |
| Gelucire 50/13 | 2–6% |

Examples IIIA and IIIB
Fexofenadine Microspheres

Microspheres were mad from the following compositions:

|   | A | B |
|---|---|---|
| Fexofenadine HCl | 50% | 65% |
| Myvaplex 600P | 40% | 30% |
| Gelucire 50/13 | 10% | 5% |

The ingredients were blended in a high shear mixer. They were then processed using the 3-inch head of Example I.

The microspheres were coated, on a Niro MP-1 Wurster fluid bed coater, with a cellulosic taste-masking coating. Dissolution of coated spheres was >80% in 30 minutes.

Other microspheres were made using various amounts of fexofenadine HCl, as follows:

| Fexofenadine HCl | 40–65% |
|---|---|
| Myvaplex 600P | 30–55% |
| Gelucire 50/13 | 5–15% |

These had properties similar to those observed above.

Example IV
Famotidine Microspheres

A spinning device of the type disclosed in U.S. Ser. No. 08/874,215, filed Jun. 13, 1997 now U.S. Pat. No. 5,851,454 and having a 3" head was used to make microspheres from the following composition:

| Famotidine | 30% |
|---|---|
| Myvaplex 600P | 65% |
| Gelucire 50/13 | 5% |

The composition was processed at about 90° C., 25% duty cycle and at 50 Hz (3000 rpm). The microspheres produced were sieved through a #40 screen and retained on a #140. They showed good morphology with few traces of fines. Dissolution tests on these spheres gave 100% drug release in 20 minutes.

The famotidine microspheres were then coated for taste masking on a Niro MP-1 fluidized bed coater with 25% coating. The coating contained a 45:55 ethyl cellulose/hydroxypropyl cellulose blend.

The coated microspheres are used in the following tablet formulation:

| Famotidine Coated microspheres | 27.8% |
|---|---|
| Floss (0.5% ethanol—See Ex. 1) | 70.2% |
| Natural Lemon flavor | 1.0% |
| Citric Acid | 0.5% |
| Syloid | 0.25% |
| Sodium Stearyl Fumarate | 0.25% |

The tablets were made on a Picola Rotary Tablet press using 9 mm flat-faced tooling at 0.5–2.0 lb. hardness and 150 mg tablet weight.

Other microspheres can be made using various amounts of famotidine, as follows:

| Famotidine | 20–30% |
|---|---|
| Myvaplex | 62.5–72.5% |
| Gelucire | 5–7.5% |

Examples VA and VB
Chlorpheniramine Microspheres

Using the device employed in Example IIB at 15% duty cycle, 60 Hz and 70°–73° C., spheres were made from compositions containing:

|   | A | B |
|---|---|---|
| Chlorpheniramine maleate | 10% | 15% |
| Myvaplex 600P | 85% | 80% |
| Gelucire 50/13 | 5% | 5% |

The microspheres produced showed, in dissolution testing, 75% drug release within 5 minutes.

Example VI

Using the device of Example IIB at 14–15% duty cycle, 60 Hz and 70°–75° C., microspheres were made from a composition containing:

| Dextromethorphan HBr | 20% |
|---|---|
| Myvaplex 600P | 70% |
| Gelucire 50/13 | 10% |

The spheres gave 75% drug release within 5 minutes when tested for dissolution. 97% of the drug dissolved in 15 minutes.

Reasonable variations, such as those which would occur to a skilled artisan, can be made herein without departing from the scope of the invention.

We claim:

1. Thermoformed compositions containing:
   (a) about 50–90% of one or more active agents, and
   (b) a combination of processing aids consisting essentially of:

(1) about 10–90% of glyceryl monostearate,
(2) about 2–15% of polyethylene glycol (32) glyceryl palmitostearate; and
(3) about 0–10% of one or more optional emulsifiers or surfactants.

2. The process of claim 1 wherein (a) contains diphenhydramine.

3. The composition of claim 2 additionally containing one or more excipients.

4. The composition of claim 3 wherein the active agent(s) is selected from the group consisting of: chlorpheniramine, cimetidine, dextromethorphan, famotidine, fexofenadine, ibuprofen, ranitidine, and salts thereof.

5. A comestible unit made from the composition of claim 4.

6. A process of making microspheres containing active agents comprising the steps:
(1) preparing a composition containing:
  (a) one or more active agents,
  (b) a combination of processing aids containing:
    (1) glyceryl monostearate, and
    (2) polyethylene glycol (32) glyceryl palmitostearate; and
    (3) one or more optional emulsifiers or surfactants;
(2) thermoforming the composition of step (1) to yield particulates, and
(3) recovering the particulates of step (2).

7. A microsphere made by the process of claim 6.

8. A process of making comestible units containing bio-affecting agents comprising the steps:
(1) preparing a composition containing:
  (a) one or more bio-affecting agents,
  (b) a combination of spheronization aids containing:
    (1) glyceryl monostearate, and
    (2) polyethylene glycol (32) glyceryl palmitostearate; and
    (3) one or more optional emulsifiers or surfactants;
(2) thermoforming the composition of step (1) to yield microparticles;
(3) recovering the microparticles of step (2);
(4) blending the microparticles with one or more excipients;
(5) shaping the blend into comestible units; and
(6) recovering the comestible units.

9. The process of claim 8 wherein (a) contains chlorpheniramine maleate.

10. The process of claim 8 wherein (a) contains cimetidine.

11. The process of claim 8 wherein (a) contains dextromethorphan HBr.

12. The process of claim 8 wherein (a) contains famotidine.

13. The process of claim 8 wherein (a) contains fexofenadine HCl.

14. The process of claim 8 wherein (a) contains ibuprofen.

15. The process of claim 8 wherein floss particles are blended with microspheres in step (4).

16. A comestible unit made by the process of claim 15.

17. The unit of claim 16 wherein (a) contains chlorpheniramine maleate.

18. The unit of claim 16 wherein (a) contains cimatidine.

19. The unit of claim 16 wherein (a) contains dextromethorphan HBr.

20. The unit of claim 15 wherein (a) contains famotidine.

21. The unit of claim 15 wherein (a) contains fexofenadine HCl.

22. The unit of claim 15 wherein (a) contains ibuprofen.

23. The process of claim 8 wherein the microparticles of step (3) are coated with one or more coatings.

24. The process of claim 23 wherein a taste masking coating is used.

25. The process of claim 23 wherein a controlled release coating is used.

26. The process of claim 8 wherein (a) contains diphenhydramine.

27. Compositions thermoformed by liquiflash processing containing:
(a) one or more active agents, and
(b) a combination of processing aids consisting essentially of:
  (1) glyceryl monostearate,
  (2) polyethylene glycol (32) glyceryl palmitostearate; and
  (3) one or more optional emulsifiers or surfactants.

28. The compositions of claim 27, wherein (a) is in the range of about 50–90%, (1) is in the range of about 10–90%, (2) is in the range of about 2–15%, and (3) is in the range of about 0–10%.

29. The compositions of claim 28, wherein (a) is in the range of about 5–90%.

* * * * *